United States Patent
Hirao

(10) Patent No.: US 8,141,420 B2
(45) Date of Patent: Mar. 27, 2012

(54) DEVICE FOR MEASURING URINE FLOW RATE

(76) Inventor: Yoshihiko Hirao, Nara (JP)

(*) Notice: Subject to any disclaimer, the term of this patent is extended or adjusted under 35 U.S.C. 154(b) by 427 days.

(21) Appl. No.: 12/294,501

(22) PCT Filed: Nov. 29, 2006

(86) PCT No.: PCT/JP2006/323759
§ 371 (c)(1),
(2), (4) Date: Nov. 25, 2009

(87) PCT Pub. No.: WO2007/111001
PCT Pub. Date: Oct. 4, 2007

(65) Prior Publication Data
US 2010/0064797 A1 Mar. 18, 2010

(30) Foreign Application Priority Data
Mar. 27, 2006 (JP) ................................. 2006-085884

(51) Int. Cl.
*G01F 15/02* (2006.01)
*G01F 23/20* (2006.01)
*G01F 19/00* (2006.01)
(52) U.S. Cl. ................. 73/198; 73/296; 73/426
(58) Field of Classification Search .................. None
See application file for complete search history.

(56) References Cited

U.S. PATENT DOCUMENTS

| 7,691,092 B2 * | 4/2010 | Corcos et al. ............ 604/318 |
| 7,722,584 B2 * | 5/2010 | Tanaka et al. ............ 604/317 |
| 2008/0004576 A1 * | 1/2008 | Tanaka et al. ............ 604/317 |

FOREIGN PATENT DOCUMENTS

| JP | 52-152892 | 11/1977 |
| JP | 59-171831 | 9/1984 |
| JP | 60-203237 | 10/1985 |
| JP | 62-203675 | 12/1987 |
| JP | 63-71008 | 5/1988 |
| JP | 2005-030788 | 2/2005 |

OTHER PUBLICATIONS

International Search Report for PCT Patent App. No. PCT/JP2006/323759 (Feb. 6, 2007).

* cited by examiner

*Primary Examiner* — Harshad Patel
(74) *Attorney, Agent, or Firm* — Cermak Nakajima LLP; Tomoko Nakajima

(57) ABSTRACT

The present invention provides an apparatus including: a container that receives urine; and a urine amount measuring device that measures the weight of the urine received by the container; wherein the urine amount measuring device has: a mounting plate, which is a plate on which the container is mounted; a measuring portion that measures the weight of the container mounted on the mounting plate multiple times at given time intervals; and an output portion that outputs a result of the measurement performed by the measuring portion, and the apparatus has a fixing structure that is situated in at least a bottom portion of the container and a mounting face of the mounting plate and that detachably fixes the container on the mounting plate.

8 Claims, 12 Drawing Sheets

FIG.6

| time (second) | urine flow amount (ml) |
|---|---|
| 0 | 0.0 |
| 1 | 0.0 |
| 2 | 5.0 |
| 3 | 20.0 |
| 4 | 33.0 |
| 5 | 37.0 |
| ⋮ | ⋮ |
| 22 | 2.5 |
| 23 | 3.1 |
| 24 | 10.0 |
| 25 | 8.0 |
| 26 | 2.4 |
| 27 | 0.0 |
| 28 | 0.0 |
| 29 | 0.0 |

DEVICE FOR MEASURING URINE FLOW RATE

TECHNICAL FIELD

The present invention relates to urine flow amount measuring apparatuses that measure a urine flow amount.

BACKGROUND ART

As apparatuses that can conveniently measure, for example, the amount of urine excreted in a unit time, so-called weight addition-type urine flow amount measuring apparatuses have been used in many conventional examples. The urine flow amount refers to a value obtained by adding, at given time intervals, the amount of urine excreted. Many of this sort of urine flow amount measuring apparatus are large installed-type apparatuses, and used in a single test performed in a facility.

Patent Document 1 has proposed a small portable urine flow rate measuring apparatus. This sort of portable urine flow rate measuring apparatus does not require a large space for storage, and can be easily carried, and thus a patient and the like can easily measure the urine flow rate at home. Accordingly, the patient does not have to be admitted to hospital or go to hospital for a urine flow rate test, and the urine flow rate test can be easily performed. Furthermore, since the urine flow rate can be measured at home, the urine excretion state in, for example, daily activities can be accurately measured. Accordingly, the urine excretion state reflecting daily activities can be evaluated. Furthermore, the urine flow rate measuring apparatus is small and does not require a large space for storage, and thus storing in hospitals or at home is easy. Furthermore, the urine flow rate measuring apparatus can be held by hand when collecting urine, and thus the position of the urine flow rate measuring apparatus can be changed during urine excretion. Accordingly, urine can be reliably received in the apparatus, and can be collected regardless of the posture of a body during urine excretion, the type of toilet bowl that is used, or the like.

[Patent Document 1] JP 2005-30788A (p. 1, FIG. 1, etc.)

DISCLOSURE OF INVENTION

Problems to be Solved by the Invention

However, in the conventional portable urine flow rate measuring apparatus, it is not possible to easily detach, replace, or wash a container in which urine is collected, or a portion that is brought into contact with urine such as a measuring portion through which urine passes. Thus, there is a problem in that keeping the urine flow rate measuring apparatus clean is difficult. For example, in a case where the container and the like are washed with water, since the urine flow amount measuring apparatus contains electrical components, the components have to be kept away from water when the apparatus is washed, and thus the apparatus cannot be sufficiently washed. This sort of washing is difficult in particular for users such as elderly people who have difficulty in performing an operation such as careful washing. As a result, washing is performed only insufficiently, and thus keeping the urine flow rate measuring apparatus clean is difficult. Moreover, there is a problem in that users end up not measuring the urine flow rate because washing the container and the like requires effort.

Furthermore, in the conventional urine flow rate measuring apparatus, urine, after measurement of the flow rate, passes through a shared measuring portion, which is not dedicated to each person subjected to the measurement, and is discharged from the lower portion of the urine flow rate measuring apparatus. Thus, there is a problem in that excreted urine cannot be collected, or that, even if urine is collected, the urine cannot be used for another test.

Furthermore, a conventional so-called weight-type urine flow amount measuring apparatus using an electronic scale does not have a structure for conveniently and reliably fixing a container that reliably receives excreted urine and a urine amount measuring device portion that measures the weight of the urine. Thus, there is a problem in that the urine flow amount measuring apparatus is not provided with a function as a portable apparatus that enables anyone to conveniently measure the urine flow amount anytime and anywhere and that can be held by one hand.

Means for Solving the Problems

The present invention is directed to a urine flow amount measuring apparatus, comprising: a container that receives urine; and a urine amount measuring device that measures the weight of the urine received by the container; wherein the urine amount measuring device comprises: a mounting plate, which is a plate on which the container is mounted; a measuring portion that measures the weight of the container mounted on the mounting plate multiple times at given time intervals; and an output portion that outputs a result of the measurement performed by the measuring portion, and the urine flow amount measuring apparatus has a fixing structure that is situated in at least a bottom portion of the container and a mounting face of the mounting plate and that detachably fixes the container on the mounting plate.

With this configuration, even if the apparatus is inclined within a certain range, urine can be reliably received. Furthermore, the container that receives urine can be easily attached, detached, and replaced, and thus a portion that receives urine can be easily kept clean. Furthermore, urine after measurement of a urine flow amount can be held in the container, and thus the urine after the measurement of the urine flow amount can be easily used again for a test and the like by detaching the container containing the urine from the urine amount measuring device.

Furthermore, in the urine flow amount measuring apparatus of the present invention, the fixing structure detachably fixes the container on the mounting plate, using a magnet.

With this configuration, even if the apparatus is inclined within a certain range, urine can be reliably received. Furthermore, the container can be easily attached to and detached from the urine amount measuring device. Moreover, with the fixing structure using a magnet, a vertical movement can be restricted.

Furthermore, in the urine flow amount measuring apparatus of the present invention, the fixing structure is constituted by a magnetic metal that is situated on the mounting face side of the container and a magnet that is situated on the mounting face side of the mounting plate.

With this configuration, the container can be easily attached to and detached from the urine amount measuring device. Furthermore, it is sufficient that a magnetic metal is situated in the bottom portion of the container, and thus the container can be manufactured at low cost. Thus, economic burden of the user in a case where the container is designed as a disposable item can be reduced.

Furthermore, the urine flow amount measuring apparatus of the present invention further comprises a protecting portion that restricts a horizontal movement of the container in a state where the container is mounted on the mounting plate.

With this configuration, a horizontal movement of the container can be restricted. Even if an impact or the like in a horizontal direction is given to the container, the container can be prevented from easily coming off.

Furthermore, the urine flow amount measuring apparatus of the present invention further comprises a holding portion that is used for holding the measuring portion.

With this configuration, the urine flow amount measuring apparatus can be easily held by hand, and thus operations when collecting urine can be easily performed.

Furthermore, in the urine flow amount measuring apparatus of the present invention, the output portion performs a given calculation on the result of the measurement performed by the measuring portion, and outputs a result of the calculation.

With this configuration, a burden for processing a measurement result obtained from the urine flow amount measuring apparatus again in another apparatus or the like can be reduced.

Furthermore, the urine flow amount measuring apparatus of the present invention further comprises a guard portion that is situated above the container along an opening portion of the container.

With this configuration, the container that receives urine can be prevented from being brought into contact with external objects, and human measurement errors caused by the contact with external objects can be avoided.

Furthermore, in the urine flow amount measuring apparatus of the present invention, an upper portion of the mounting plate has a projection face, a bottom face of the container is a recess face, and the recess face is mounted so as to cover the projection face of the mounting plate.

With this configuration, even if the apparatus is inclined within a certain range, the container practically does not come off the mounting plate because the projection face of the upper portion of the mounting plate and the recess face of the bottom face of the container are brought into contact with each other, and thus urine can be reliably received. Accordingly, measurement errors caused by a weight change due to a movement of the container that receives urine can be minimized.

EFFECT OF THE INVENTION

With the urine flow amount measuring apparatus according to the present invention, a portion that receives urine can be easily kept clean. Furthermore, urine after measurement of a urine flow amount can be easily used again for a test and the like.

BEST MODE FOR CARRYING OUT THE INVENTION

Hereinafter, an embodiment of a urine flow amount measuring apparatus will be described with reference to the drawings. It should be noted that constituent elements denoted by the same reference numerals in the embodiment perform similar operations, and thus a description thereof may not be repeated.

BRIEF DESCRIPTION OF THE DRAWINGS

FIG. 6 is a diagram for illustrating a measurement result of the urine flow amount measuring apparatus in this embodiment.

EMBODIMENTS

Figure 1:
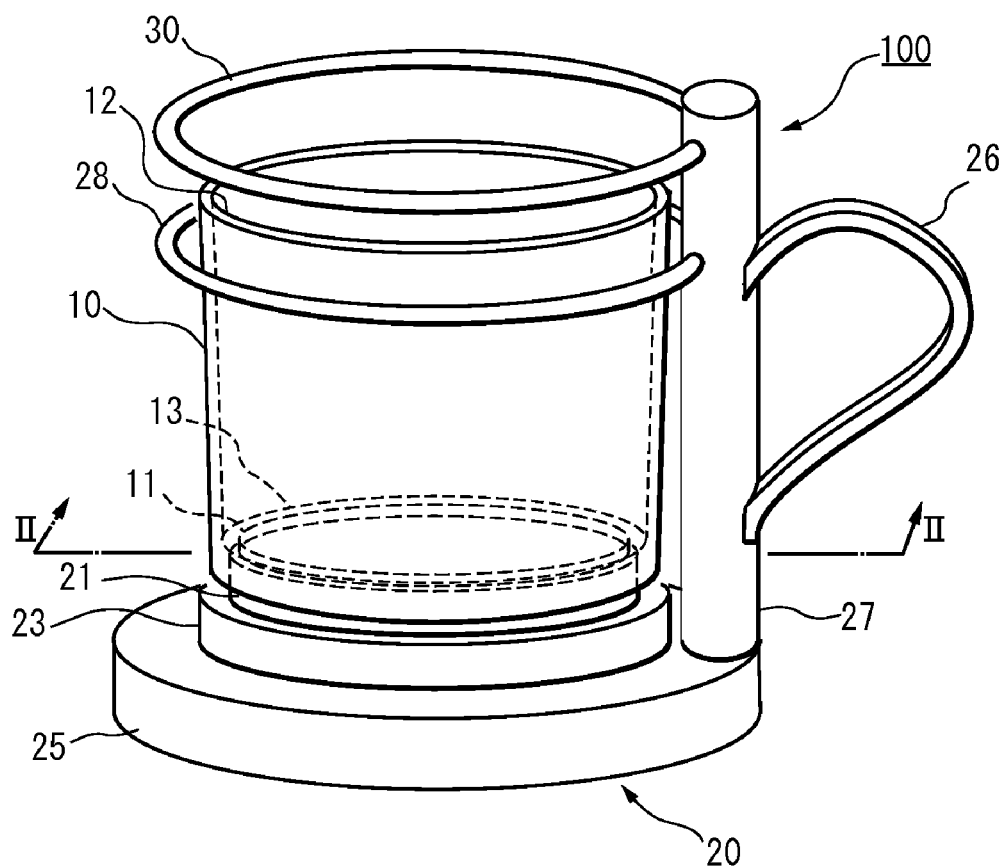
FIG. 1 is a perspective view of a urine flow amount measuring apparatus according to an embodiment.

FIG. 1 is a perspective view for illustrating the structure of a urine flow amount measuring apparatus according to this embodiment.

Figure 2:
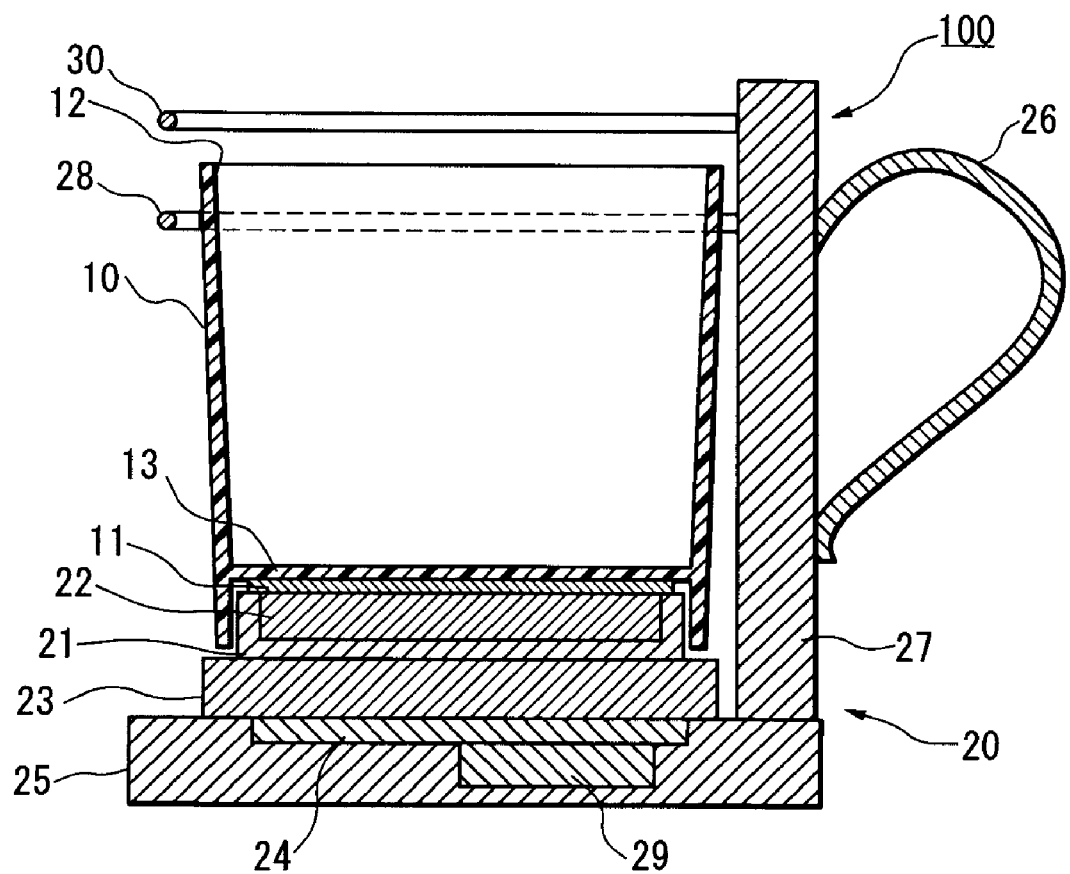
FIG. 2 is a cross-sectional view of the urine flow amount measuring apparatus in this embodiment.

FIG. 2 is a cross-sectional view for illustrating the structure of the urine flow amount measuring apparatus according to this embodiment, taken along line II-II in FIG. 1.

Figure 3A:
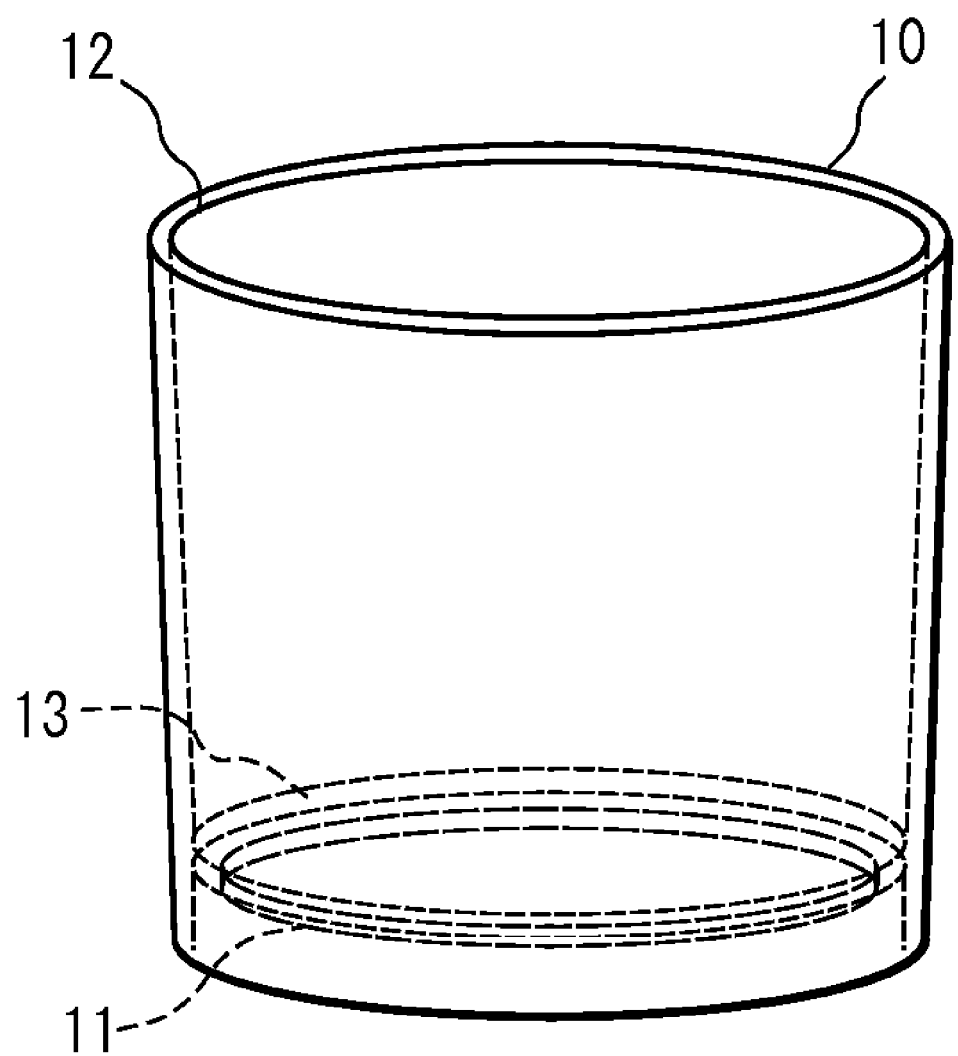
FIG. 3a is a perspective view from above showing a container of the urine flow amount measuring apparatus in this embodiment.
Figure 3B:
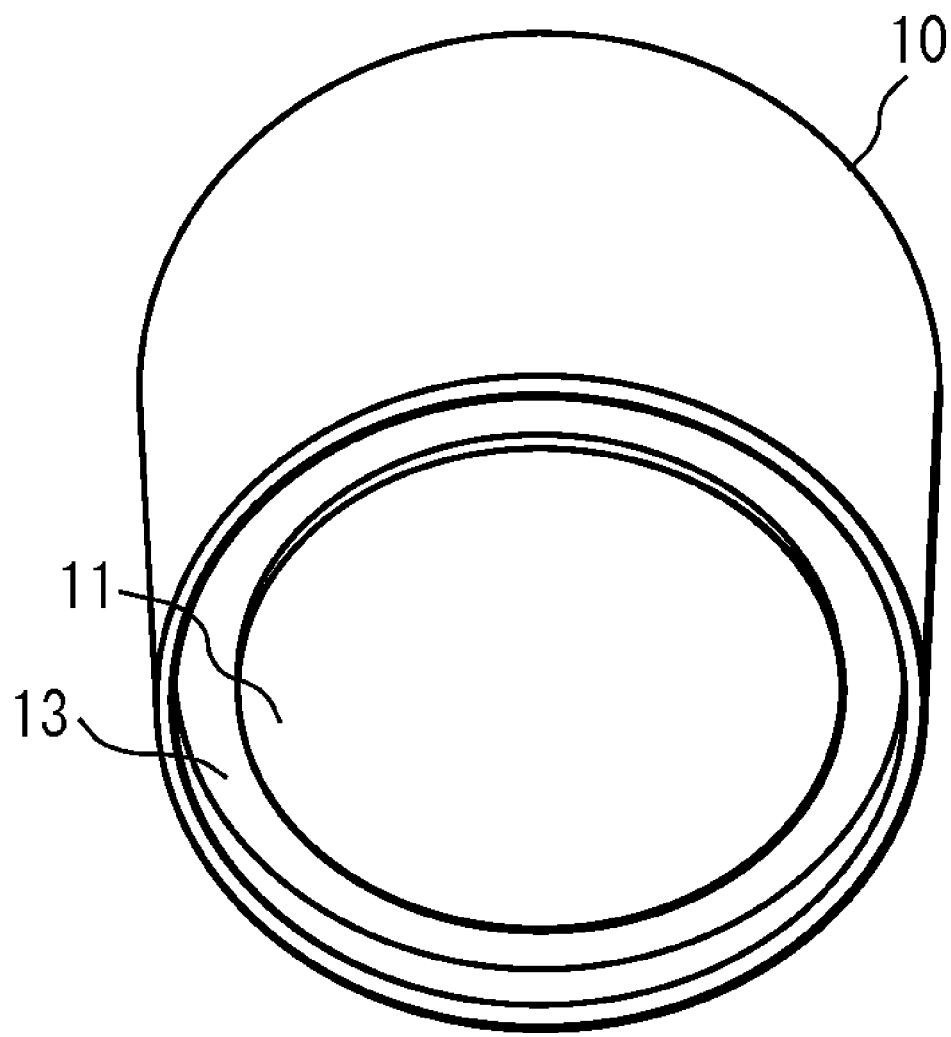
FIG. 3b is a perspective view from below showing the container of the urine flow amount measuring apparatus in this embodiment.

FIGS. 3a and 3b are a perspective view viewed from above (FIG. 3a) and a perspective view viewed from below (FIG. 3b) for illustrating the structure of a container of the urine flow amount measuring apparatus according to this embodiment.

Figure 4:
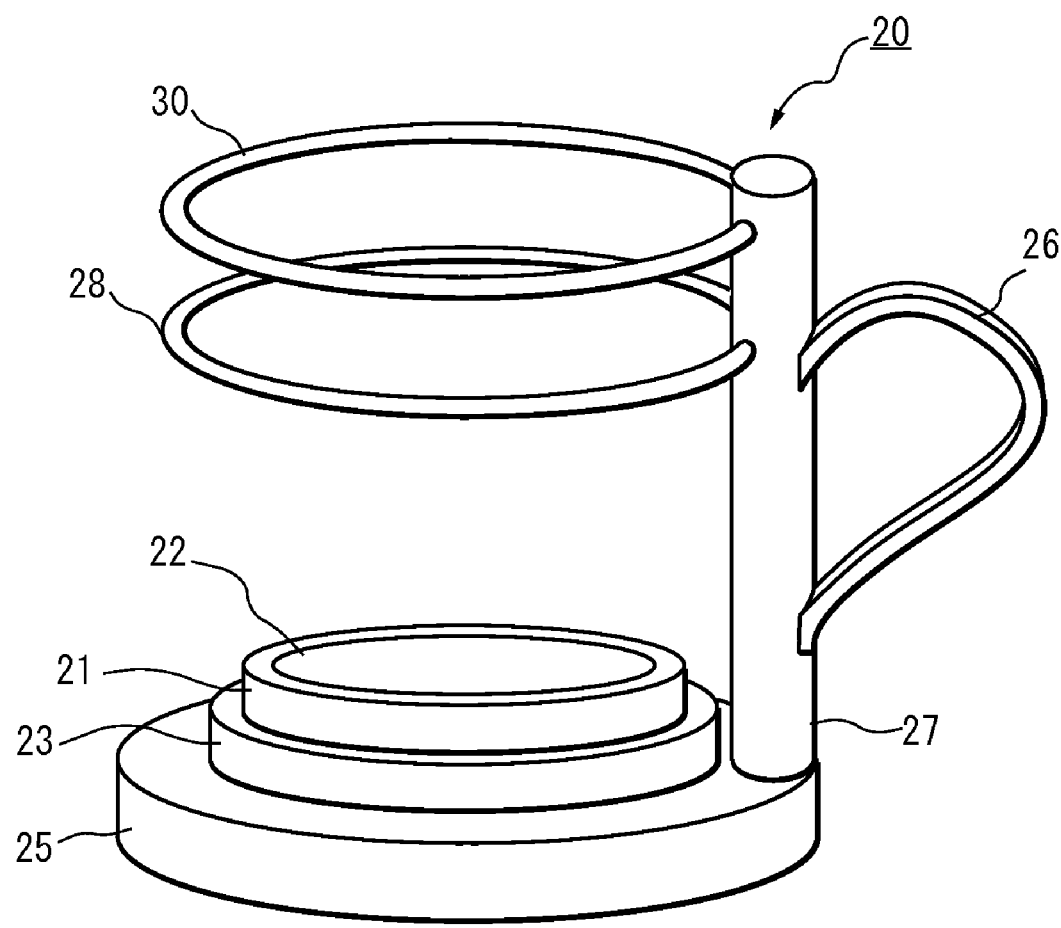
FIG. 4 is a perspective view of a urine amount measuring device of the urine flow amount measuring apparatus in this embodiment.

FIG. 4 is a perspective view for illustrating the structure of a urine amount measuring device of the urine flow amount measuring apparatus according to this embodiment.

A urine flow amount measuring apparatus 100 according to this embodiment includes a container 10 that receives urine and a urine amount measuring device 20 that measures the weight of the urine received by the container 10. The urine flow amount measuring apparatus 100 according to this embodiment is a portable urine flow amount measuring apparatus, and has a height of, for example, approximately 10 to 12 cm.

The container 10 further includes a magnetic metal 11.

Furthermore, the urine amount measuring device 20 includes a mounting plate 21, a magnet 22, a measuring portion 23, an output portion 24, a fixing plate 25, a holding portion 26, a protecting portion 28, an electric power supply portion 29, and a guard portion 30.

The container 10 receives urine. More specifically, the container 10 has a lower portion including a bottom portion 13 and an upper portion including an opening portion 12, and urine excreted from a human body is received via the opening portion 12. Any material can be used as the material of the container 10, as long as urine can be contained. For example, paper, a resin such as plastic, or a metal such as aluminum may be used. For example, if the material is plastic or the like, the container 10 can be manufactured at low cost by using a plastic molding technique. The surface (inner face) of the material may be subjected to surface treatment for providing a waterproofing effect or the like, or may be coated. It is preferable that the material of the container 10 is a disposable or recyclable, and a low-cost material. There is no limitation on the shape of the container 10, but it is preferable that the diameter of the opening portion 12 is sufficiently large so that urine can be easily received. For example, it is preferable that the diameter of the opening portion 12 is approximately 10 to 14 cm. Herein, as the container 10, a container in which the diameter of the opening portion 12 is larger than that of the bottom portion side is used. The urine flow amount measuring apparatus 100 of this embodiment is a portable apparatus that can be used when held by a hand, and urine can be collected in a state where the container 10 is brought close to the external urethral opening. Thus, the opening portion 12 of the container 10 can be made sufficiently smaller than a portion that receives urine in an installed-type urine flow amount measuring apparatus, and urine can be reliably collected without fear of spillage of urine out of the container 10. Furthermore, it is preferable that the capacity of the container 10 is a capacity with which urine excreted in a single occasion by an ordinary adult can be sufficiently received, and is, for example, 800 ml or more. Furthermore, it is preferable that the height of the container 10 from the bottom portion 13 to the upper end of the container 10 is approximately 7 to 10 cm. The magnetic metal 11 is situated on the lower face side of the bottom portion 13 of the container 10. Any material can be used as the material of the magnetic metal 11, as long as it is attracted by a magnet. For example, iron, nickel, their alloys, their compounds, and the like are conceivable. Herein, the magnetic metal 11 is a film constituted by a thin iron layer such as a metal foil, and is attached to the bottom portion 13. However, there is no limitation on the shape of the metal 11. For example, the metal 11 may be a line-shaped metal, or may be a metal piece. Furthermore, the metal 11 may be bonded with an adhesive or the like, or may be fitted to or embedded in the bottom portion 13. Alternatively, the metal 11 may be attached using a tape or the like. Alternatively, the metal 11 may be a powdered metal applied or sprayed together with a substance such as an adhesive or paint. Furthermore, the metal 11 does not absolutely have to be exposed on the lower face of the bottom portion. The surface of the metal 11 may be covered by a material such as a seal or a film, or the metal 11 may be held or embedded in the material of the bottom portion 13 or may be situated on the upper face side of the bottom portion 13, that is, on the interior side of the container 10. The metal 11 may be situated in any manner as long as it is situated at least in the bottom portion 13, and it may extend also to a portion other than the bottom portion 13. For example, the metal 11 may be situated on the entire external face of the container. Herein, for example, the bottom portion 13 of the container 10 is positioned higher than the lower end of the bottom portion 13 of the container 10, and the side face of the container 10 and the lower portion of the side face define a recess portion. However, the bottom portion 13 and the lower end of the side face of the container 10 also may be positioned at substantially the same height.

The mounting plate 21 is a plate on which the container 10 is mounted. The magnet 22 is situated on the mounting face side of the mounting plate 21, which is a face on which the container 10 is mounted. When the bottom portion 13 of the container 10 is mounted on the mounting face of the mounting plate 21, the magnetic metal 11 situated in the bottom portion 13 of the container 10 is attracted by the magnet 22 of the mounting plate 21, and thus the container 10 is detachably fixed to the urine amount measuring device 20. This sort of structure for detachably fixing the container 10 on the mounting plate 21, the structure being situated in the bottom portion 13 of the container 10 and the mounting face of the mounting plate 21, is referred to as a fixing structure. Herein, as the fixing structure, a fixing structure using a magnet is used. For example, the metal 11 and the magnet 22 correspond to the fixing structure. The magnet 22 may be a permanent magnet, or may be an electromagnet. The magnet 22 has to have a magnetic force that can attract the metal 11. The magnet 22 may be externally exposed, or may not be exposed, on the mounting face of the mounting plate 21. Furthermore, the entire mounting plate 21 may be constituted by a magnet. The entire mounting face of the mounting plate 21 may be constituted by a magnet. Herein, the fixing structure using a magnet was shown as an example, but the fixing structure may be any structure, as long as the container 10 can be easily attached to and detached from the mounting plate 21. For example, a structure may be applied in which faces of the container 10 and the mounting plate 21 opposing each other respectively have a hook face and a loop face of hook-and-loop fasteners such as Magic Tape (registered trademark). Accordingly, when the container 10 is simply mounted on the mounting plate 21, the container 10 can be fixed onto the mounting plate 21. Furthermore, when the container 10 is pulled with a slight force in the opposite direction from the mounting plate 21, the container 10 can be detached from the mounting plate 21. Moreover, the fixing structure may be constituted by a smooth bottom face of the container 10 and a suction cup attached to the upper face of the mounting plate 21. In this case, when the container 10 is pressed with a slight force against the suction cup on the mounting plate 21, the container 10 can be fixed onto the mounting plate 21. Furthermore, when the container 10 is pulled with a slight force in the opposite direction from the mounting plate 21, the container 10 can be detached from the mounting plate 21. It is preferable that the fixing structure is a structure in which the container 10 can be fixed by simply being mounted on the mounting plate 21, such as a structure using a magnet or a structure using hook-and-loop fasteners as described above, because attachment is easy and attachment errors practically do not occur. For example, in the case of a fixing structure using a suction cup or the like, if the force to press the container 10 for mounting is insufficient, the container 10 may come off during measurement of a urine flow amount. It is particularly preferable that the fixing structure is a structure using a magnet. In the case of a structure using a magnet, the container 10 can be fixed by simply being mounted on the mounting plate 21. Unlike a fixing structure using hook-and-loop fasteners or the like, the structure using a magnet uses a magnetic force for fixing, and thus the upper face of the mounting plate 21 and the bottom face of the container 10 can be flat without having a rough face. As a result, dirt and the like can be easily wiped off, and thus the container 10 and the mounting plate 21 can be kept clean. Herein, the diameter of the mounting plate 21 is smaller than the diameter of the recess portion in the lower portion of the container 10, and the height of the mounting plate 21 is larger than the depth of the recess portion in the lower portion of the container 10. That is to say, the upper portion of the mounting plate 21 is a projection portion. When the container 10 is positioned so that the recess portion in the lower portion covers the mounting plate 21, the metal 11 is attracted by the magnet 22, and the mounting plate 21 is fitted to the recess portion in the lower portion of the container 10. Accordingly, for example, when the urine flow amount measuring apparatus 100 is being used when held by a hand, even if a horizontal force acts on the container 10 due to a movement of the hand, force of urinary stream during urine excretion, or the like, the side face of the container 10 near the lower end is brought into contact with the side face of the mounting plate 21. Thus, a horizontal movement of the container 10 can be restricted, and the container 10 can be prevented from coming off the urine amount measuring device 20. In particular, since the urine flow amount measuring apparatus 100 of this embodiment is portable and measures a urine flow amount when held by a hand, the container 10 may hit an obstacle such as a toilet bowl hard. However, also in this case, the recess portion in the lower portion of the container 10 prevents the container 10 from easily coming off.

The measuring portion 23 measures the weight of the container 10 mounted on the mounting plate 21 and urine received in the container 10 multiple times at given time intervals. More specifically, the measuring portion 23 measures the weight of the mounting plate 21, the container 10, and urine received in the container 10. However, if the weight measured in a state where the mounting plate 21 is attached is set to 0 in advance, the measuring portion 23 can measure the weight of the container 10 and urine received in the container 10. Furthermore, a measured value may be set so that the weight measured in a state where the container 10 is attached is 0. In this case, the measuring portion 23 can measure the amount of only urine. Herein, the amount of urine is measured as weight, but the amount of urine also may be considered as volume as appropriate in consideration of the specific gravity of urine. The measuring portion 23 is constituted by, for example, a weighing sensor, a calculating portion such as an MPU that obtains a measurement result of the weight using output from the weighing sensor, a memory, and the like. The mounting plate 21 may be considered as a plate on which an object that is to be measured by the measuring portion 23 is mounted. The measuring portion 23 may have the configuration of an apparatus such as an ordinary electronic scale that can measure weight or mass using a weighing sensor. This configuration is a known art, and thus a description thereof has been omitted. For example, an electronic scale or the like capable of measuring the weight up to approximately 1 kg can typically distinguish between values of approximately 10 mg in the measurement, and one droplet of urine is approximately 50 mg. Thus, if the configuration of this sort of electronic scale is applied to the measuring portion 23, the urine flow amount can be accurately measured. Here, 'given time intervals' may be regular intervals, or may be irregular intervals. For example, given time intervals may be approximately 0.5 to 1 second. Furthermore, there is no limitation on the number of times of the measurement performed by the measuring portion 23, as long as the measurement is performed multiple times. Here, the measurement preferably does not end until urine excretion ends. The measurement by the measuring portion 23 may start at a time point when the power of the urine flow amount measuring apparatus 100 is turned on, or at a time point when the measuring portion 23 detects the container 10 receiving the first droplet of urine after the power is turned on. It is preferable that, in the measuring portion 23, the weight measured in a state where the mounting plate 21 is attached is set to 0 in advance. Furthermore, a measured value may be set so that the weight measured in a state where the container 10 is attached is 0. The measuring portion 23 includes, for example, a timer device, and simultaneously records the measurement time.

The fixing plate 25 is a plate for fixing the measuring portion 23 in a state where the measuring portion 23 is mounted on the upper face of the fixing plate 25. The width of the fixing plate 25 is, for example, approximately 15 to 17 cm. In a case where the output portion 24 and the electric power supply portion 29 described later do not have to be arranged inside the fixing plate 25, for example, if these constituent elements can be arranged inside the measuring portion 23, the fixing plate 25 may be omitted.

The output portion 24 outputs a result of the measurement performed by the measuring portion 23. For example, the output portion 24 wirelessly transmits the measurement result to another apparatus or the like (not shown) outside the urine flow amount measuring apparatus 100. Also, the measurement result may be transmitted via a wired connection to another apparatus or the like (not shown). The output portion 24 may transmit each measurement result each time the measurement result is obtained, or may temporarily accumulate measurement results in a memory or the like and transmit all accumulated measurement results at a time point when the measurement completely ends, or if an accepting portion or the like (not shown) accepts an instruction to transmit measurement results. The output portion 24 may be realized, for example, as a combination of driver software for an output device and the output device. For example, the output portion 24 is realized by means of wireless communications, more specifically, communications using wireless LAN or the like, or short-range wireless communications using Bluetooth (registered trademark) or the like, for example. Alternatively, the output portion 24 may be realized by means of wireless broadcasting. Furthermore, the output portion 24 may output a measurement result to a memory or the like such as a non-volatile memory situated inside the urine flow amount measuring apparatus 100, and accumulate detection signals in this memory or the like. In this case, this memory may be a so-called memory card that can be removed from the urine flow amount measuring apparatus 100, and measurement results accumulated in this memory card may be read also by another apparatus. Furthermore, the accumulated measurement results may be transmitted via a wired or wireless connection in a single batch to another apparatus. Here, 'output' has a concept that includes, for example, transmission to an external apparatus and accumulation in a storage medium or the like. Furthermore, the output portion 24 may have an antenna or the like (not shown) used to transmit measurement results. Herein, the output portion 24 is situated inside the fixing plate 25. There is no limitation, for example, on the position at which the output portion 24 is situated. For example, the output portion 24 may be situated inside the measuring portion 23.

The electric power supply portion 29 supplies electric power. More specifically, the electric power supply portion 29 supplies electric power to the measuring portion 23 and the output portion 24. Furthermore, in a case where the magnet 22 is an electromagnet, electric power is supplied also to this magnet. Turning on and off of electric power supply by the electric power supply portion 29 is controlled by a switching element or the like (not shown). The electric power supply portion 29 can be realized, for example, as a battery, a combination of a battery and a switching element, or the like. This battery may be rechargeable, or may not be rechargeable. There is no limitation on the type of the battery, and it is possible to use a lithium battery and the like. It is preferable that the battery is small and can supply electric power for a long period of time. The electric power supply portion 29 may supply electric power that is supplied from an external power source, but it is preferable that a power source such as a battery is contained inside the urine flow amount measuring apparatus 100 in order to make the urine flow amount measuring apparatus 100 portable. Herein, it is assumed that the electric power supply portion 29 is situated inside the fixing plate 25. Here, there is no limitation, for example, on the position at which the electric power supply portion 29 is situated. For example, the electric power supply portion 29 may be situated inside the measuring portion 23.

The holding portion 26 is used for holding the urine flow amount measuring apparatus 100. With the holding portion 26, the urine flow amount measuring apparatus 100 can be easily held by hand, and urine can be easily collected during measurement of a urine flow amount. Herein, the holding portion 26 has an attachment member 27, which is a rod-like member for attaching the holding portion 26 to the urine amount measuring device 20, and one end of the attachment member 27 is attached to part of the peripheral portion of the fixing plate 25 so that the one end is substantially perpendicular to the surface of the fixing plate. There is no limitation on the structure of the holding portion 26, as long as the urine amount measuring device 20 of the urine flow amount measuring apparatus 100 can be held and measurement of a urine flow amount performed by the measuring portion 23 is not hampered. Furthermore, there is no limitation on how the holding portion 26 is attached to the urine amount measuring device 20. For example, one end of the attachment member 27 of the holding portion 26 may be fixed to the measuring portion 23.

The protecting portion 28 eliminates any external force applied to the container 10 in a state where the container 10 is fixed to the urine amount measuring device 20. Herein, the protecting portion 28 is a wire-like member formed in the shape of a ring positioned around the upper portion of the container 10, and is fixed to the upper portion of the holding portion 26. With the protecting portion 28, for example, when the urine flow amount measuring apparatus 100 is being used when held by a hand, even if a strong horizontal force acts on the container 10 due to a movement of the hand, large inclination, or the like, the side face of the upper portion of the container 10 is brought into contact with the side face of the protecting portion 28. Thus, a horizontal movement of the container 10 can be restricted, and the container 10 can be prevented from coming off the urine amount measuring device 20. In particular, since the urine flow amount measuring apparatus 100 of this embodiment is portable and measures a urine flow amount when held by a hand, the container 10 may hit an obstacle such as a toilet bowl hard. Also in this case, with the protecting portion 28, a protection effect can be provided so that the container 10 practically does not hit an obstacle, and the container 10 can be prevented from easily coming off even if the container 10 hits an obstacle. There is no limitation on the structure, the material, and the like of the protecting portion 28, as long as a horizontal movement of the container 10 can be restricted and attachment and detachment of the container 10 are not hampered. For example, the protecting portion 28 may be a belt-like member in the shape of a ring having a given width. Alternatively, the protecting portion 28 may be a member in the shape of a ring that is partially cut away.

The guard portion 30 is situated above the container 10 along the opening portion of the container 10. However, the guard portion 30 does not have to be positioned accurately along the opening portion of the container 10, and there is no limitation on its shape. The guard portion 30 is positioned so as not be brought into contact with the container 10. Herein, the guard portion 30 is attached to the attachment member 27. The guard portion 30 is for preventing the container 10 that receives urine from being brought into contact with external objects such as clothes. With the guard portion 30, an impact or the like caused by the contact between the container 10 that receives urine and external objects can be reduced, and human measurement errors can be avoided.

Next, the operation of measuring the urine flow amount using the urine flow amount measuring apparatus 100 will be described.

Figure 5:
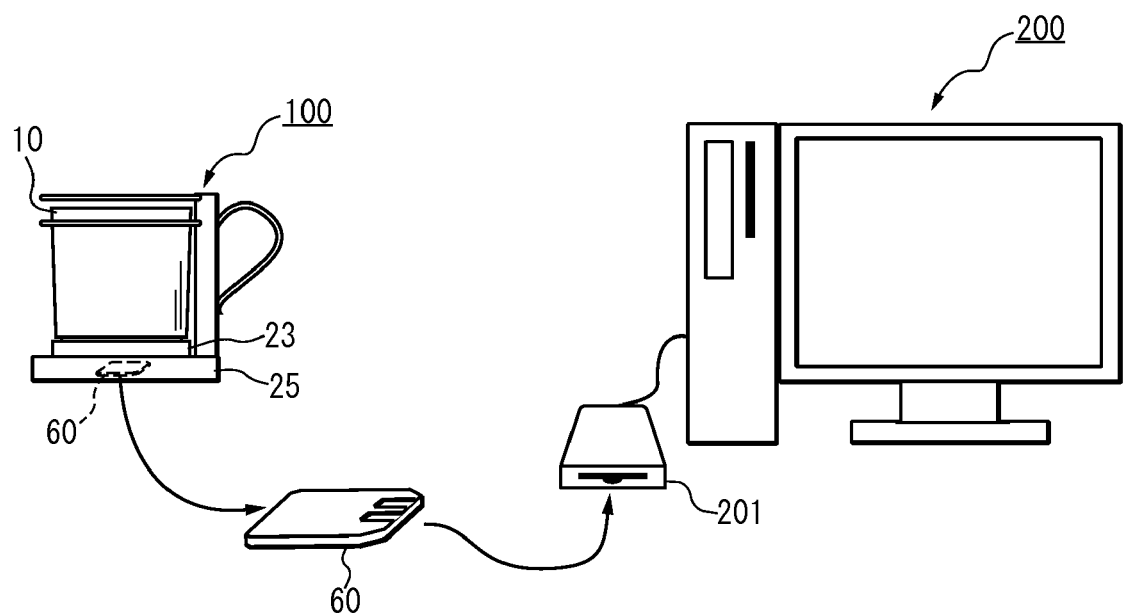
FIG. 5 is a schematic view of a system including the urine flow amount measuring apparatus in this embodiment.

FIG. 5 is a schematic view showing the configuration of a urine flow amount measuring system including the urine flow amount measuring apparatus 100. This urine flow amount measuring system includes the urine flow amount measuring apparatus 100 and an information processing apparatus 200. It is assumed that, although not shown, the information processing apparatus 200 includes an accepting portion that accepts a measurement result of a urine flow amount acquired by the urine flow amount measuring apparatus 100, an accumulating portion that accumulates the measurement result accepted by the accepting portion in a memory or the like, a processing portion that performs a given process on the measurement result accepted by the accepting portion, and an output portion that outputs, for example, displays a result of this process, and the like. The configuration of the information processing apparatus in which information indicating measurement results from various measuring apparatuses are accepted, accumulated, and subjected to a given process and the like is a known art, and thus a description thereof has been omitted. Herein, it is assumed that the urine flow amount measuring apparatus 100 internally includes a memory card 60, which is a removable flash memory, and the output portion 24 accumulates measurement results from the measuring portion 23 in the memory card 60. Furthermore, if the memory card 60 is removed from the urine flow amount measuring apparatus 100 and attached to the memory card reader 201 of the information processing apparatus 200 so that the accumulated information is read by a memory card reader 201, the measurement result acquired by the urine flow amount measuring apparatus 100 can be acquired, accumulated, subjected to a given process, and output by the information processing apparatus 200. The configuration in which information is to be read from or written onto a memory card or the like, such as the configuration or the process of a memory card reader or a memory card writer, is a known art, and thus a description thereof has been omitted. The information processing apparatus 200 may include a unit that performs wireless communications using Bluetooth or the like, and the output portion 24 of the urine flow amount measuring apparatus 100 may transmit a result of measurement performed by the measuring portion 23 via wireless communications to the information processing apparatus 200.

First, from above the urine amount measuring device 20 shown in FIG. 4 through the protecting portion 28, the container 10 is mounted on the mounting plate 21 so that the bottom portion 13 of the container 10 is positioned on the mounting face of the mounting plate 21. If the container 10 is mounted in this manner, the magnet 22 attracts the metal 11, and the container 10 is fixed onto the mounting plate 21. This fixing is realized with a magnet, and thus a hooking process or the like is not necessary at the time of fixing, and thus attachment is easy. Furthermore, the container 10 can be easily detached with application of a slight force.

Next, if a switch or the like (not shown) is operated to turn the power of the urine flow amount measuring apparatus 100 on, measurement of a urine flow amount starts. Herein, when the power is turned on, or if the user gives an instruction to an accepting portion or the like (not shown) by pressing a button or the like (not shown), the measuring portion 23 performs a so-called zero-point adjustment in which a reference point during measurement is adjusted so that the value measured by the measuring portion 23 in a state where the container 10 is attached is 0. However, such a zero-point adjustment does not absolutely have to be performed. There is no limitation on a trigger to start the measurement.

Herein, for example, it is assumed that the measuring portion 23 measures the weight once every second, and the output portion 24 sequentially accumulates measurement results from the measuring portion 23 in a memory card together with information indicating the time elapsed after the start of the measurement. If the user holds the urine flow amount measuring apparatus 100 by hand at the holding portion 26, and urine is excreted in the container 10, the total weight of excreted urine is measured by the measuring portion 23 once every second after the start of the measurement, and the measurement results are sequentially accumulated in the memory card together with information indicating the time elapsed after the start of the measurement. Herein, the magnet 22 attracts the metal 11 and thus the container 10 is fixed onto the mounting plate 21. Accordingly, when urine is collected in a state where the user holds the urine flow amount measuring apparatus 100 by hand at the holding portion 26, the container 10 does not move away from the fixed position, come off, or partially move upward, and thus the urine flow amount can be accurately measured.

FIG. 6 is a diagram showing measurement results of the urine flow amount accumulated in the memory card. The measurement results have the attributes 'time' and 'urine flow amount'. Here, 'time' refers to the time elapsed after the measurement is started, that is, after the power is turned on. In this example, 'time' is indicated in seconds. 'Urine flow amount' refers to the result of measurement performed by the measuring portion 23. Since the measuring portion 23 measures the weight, it is a weight value that is actually acquired as the measurement result. However, in this example, since an object that is to be measured is urine, which is a liquid, 1 g of urine is converted into 1 ml of urine, and the urine flow amount in milliliters is accumulated. For the sake of simplicity, it is assumed that the urine flow amount is measured to one decimal place in milliliters. 'Urine flow amount' refers to the total weight of urine obtained between measurement timings.

If the user ends urine excretion and operates a switch or the like (not shown) to turn the power off, the measurement of the urine flow amount ends. Herein, as shown in FIG. 6, the power is turned off at a time point when 29 seconds have elapsed after the power is turned on.

The user detaches the container 10 containing urine from the urine flow amount measuring apparatus 100. Herein, the used container 10 is disposed of after disposal of the urine. At the time of the next urine measurement, a new container 10 is used. The used container 10 may be collected, washed, sterilized, and reused. Furthermore, the detached container 10 containing urine also can be used as it is, as a sample for a urine test and the like.

Figure 7:
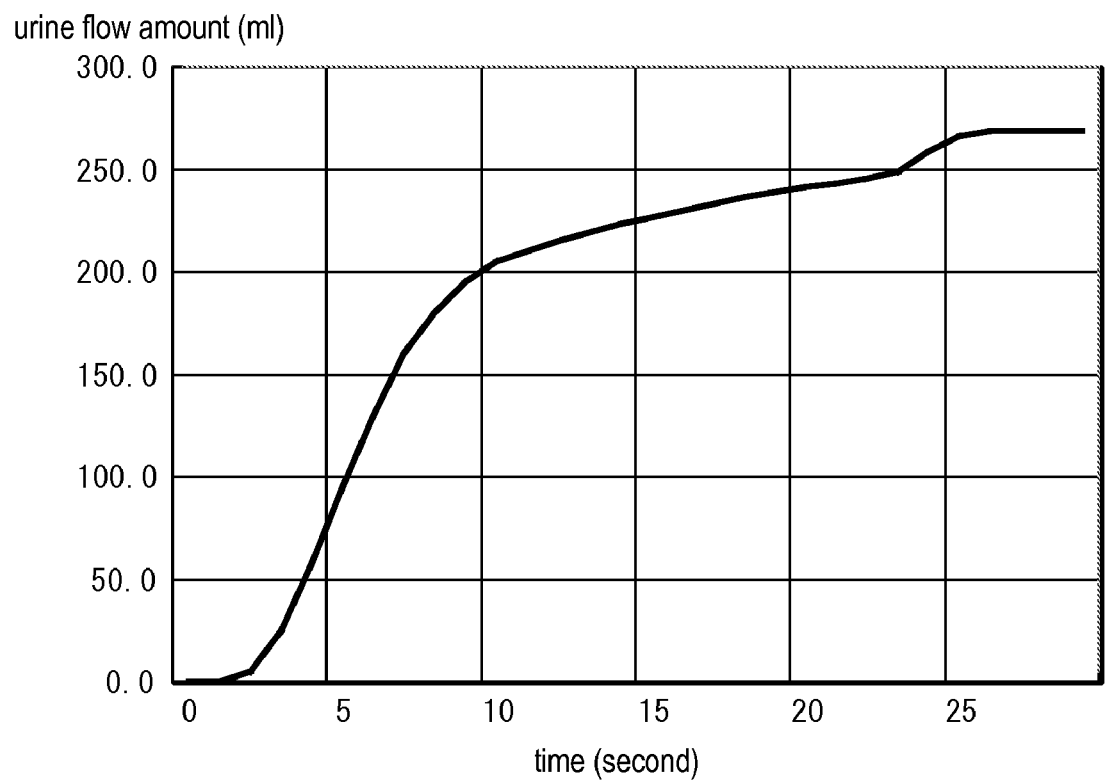
FIG. 7 is a graph showing a display example in this embodiment.
Figure 8:
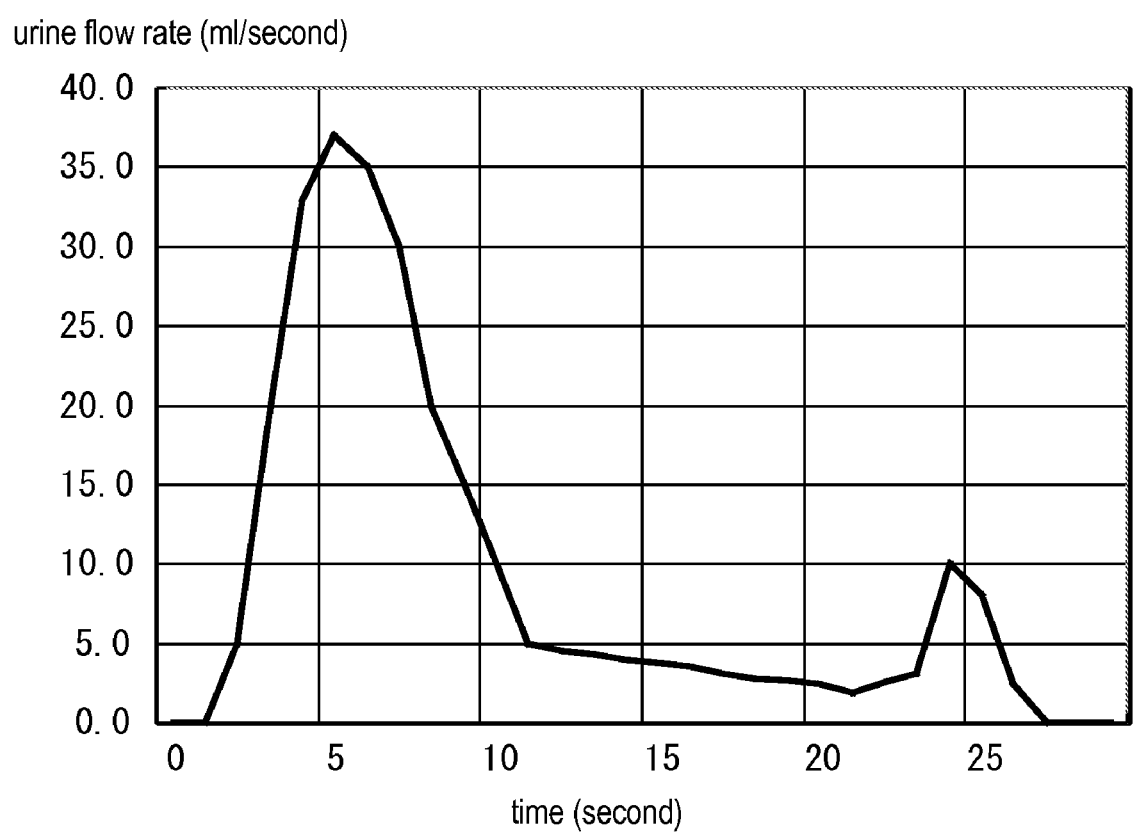
FIG. 8 is a graph showing a display example in this embodiment.

Next, the memory card 60 is removed from the urine flow amount measuring apparatus 100 and attached to a memory card reader or the like (not shown) of the information processing apparatus 200, so that information in the memory card as shown in FIG. 6 is read. In the information processing apparatus 200, a given process is performed based on the read information. For example, as shown in FIG. 7, a graph of the urine flow amount may be output to a display or the like. The urine flow amount per second, that is, the urine flow rate may be obtained by subtracting a urine flow amount value one second before from a urine flow amount value measured at each timing, and output as shown in FIG. 8. Furthermore, the time during which urine is actually excreted (26 seconds, in this example) may be calculated by detecting the time at which the urine flow rate is changed from 0 and the time at which the urine flow rate is changed to 0 and obtaining the length of the time between them, the average urine flow rate, which is an average of the urine flow rate, may be obtained, and the obtained results may be output to a display or the like. Furthermore, the graphs, information obtained with calculation or other processing, and the like may be printed, accumulated in a storage medium or the like, or transmitted to another apparatus, instead of being displayed.

As described above, in this embodiment, the container 10 is detachably fixed to the mounting plate 21 by the fixing structure. Thus, the container 10 can be easily attached to and detached from the urine amount measuring device 20. Accordingly, for example, the used container 10 can be disposed of or collected, and replaced by a new container 10 each time the urine flow amount is measured, and thus the urine flow amount measuring apparatus 100 can be always kept clean without effort-requiring washing process and the like. Thus, even people who cannot perform effort-requiring operations, such as elderly people or physically disabled people, can easily keep the urine flow amount measuring apparatus 100 clean. Moreover, effort-requiring operations can be reduced also for medical workers. Furthermore, also in a case where the container 10 is washed and reused, since the container 10 does not include an electrically operating device or the like, the entire the container 10 can be washed without limiting portions that are to be washed. Thus, the wash operation can be easily performed, and the entire container 10 can be kept clean.

Furthermore, since the container 10 is detachably fixed by the fixing structure constituted by the metal 11 and the magnet 22, the container 10 can be easily attached or detached, and the container 10 can be promptly replaced. Furthermore, since the container 10 is attached by simply being mounted on the mounting plate 21, attachment errors practically do not occur. Thus, the user can replace the container 10 without performing a special practice or the like. Also, even elderly people or physically disabled people who cannot perform careful attachment operations or the like can easily replace the container 10. Furthermore, when having an urge to urinate, the user can reliably attach the container 10 to the urine amount measuring device 20 in a short time. Thus, a situation can be prevented in which the user feels stressed due to difficulty in attaching the container 10 and thus an accurate measurement result cannot be obtained, the urine flow amount is measured in a state where the container 10 is not completely attached and thus the container 10 comes off during the measurement, or the container 10 cannot be attached in time for urine excretion and thus the urine flow amount cannot be measured.

Furthermore, since the container 10 is detachably fixed by the fixing structure constituted by the metal 11 and the magnet 22, it is possible to prevent a situation in which the container 10 comes off or partially moves upward from the urine amount measuring device 20 due to a movement of the hand, an impact or the like applied when urine is received in the container, or the like, when the urine flow amount is measured in a state where the urine flow amount measuring apparatus 100 is held by a hand. Thus, an accurate urine flow amount can be measured. In particular, in the case of the urine flow amount measuring apparatus 100 that can be used when held by a hand, the urine flow amount measuring apparatus 100 cannot always be kept substantially horizontal, or is difficult to fix at a constant position, unlike a so-called installed-type urine flow amount measuring apparatus or the like installed, for example, on the floor for use, and thus the container 10 may come off the urine amount measuring device 20 due to a movement of the hand. Furthermore, urine is received in a state where the urine flow amount measuring apparatus 100 is inclined without being kept horizontal, and thus the container 10 may come off the urine amount measuring device 20 due to a force applied from an unexpected direction when urine is received. Accordingly, accurate measurement may not be performed. However, in this embodiment, with this sort of fixing structure, the problem can be solved that the urine flow amount is not accurately measured due to the container 10 coming off or attachment becoming unstable.

Furthermore, in this embodiment, urine is received in the container 10, and thus the urine can be used for another test and the like.

Furthermore, in this embodiment, it is sufficient that the magnetic metal 11 such as a metal foil is situated in the bottom portion 13 of the container 10, and thus the container 10 can be manufactured at low cost. Thus, economic burden of the user in a case where the container 10 is designed as a disposable item can be reduced.

Furthermore, in this embodiment, the container 10 may have a permanent magnet instead of the metal 11, and the mounting plate 21 may have a dielectric metal instead of the magnet 22.

Furthermore, in this embodiment, the output portion 24 may perform processes performed by the information processing apparatus 200 such as the process of calculating the urine flow rate, the average urine flow rate, or the like based on the measurement result acquired by the measuring portion 23, and output information obtained as a result of the processes.

Figure 9:
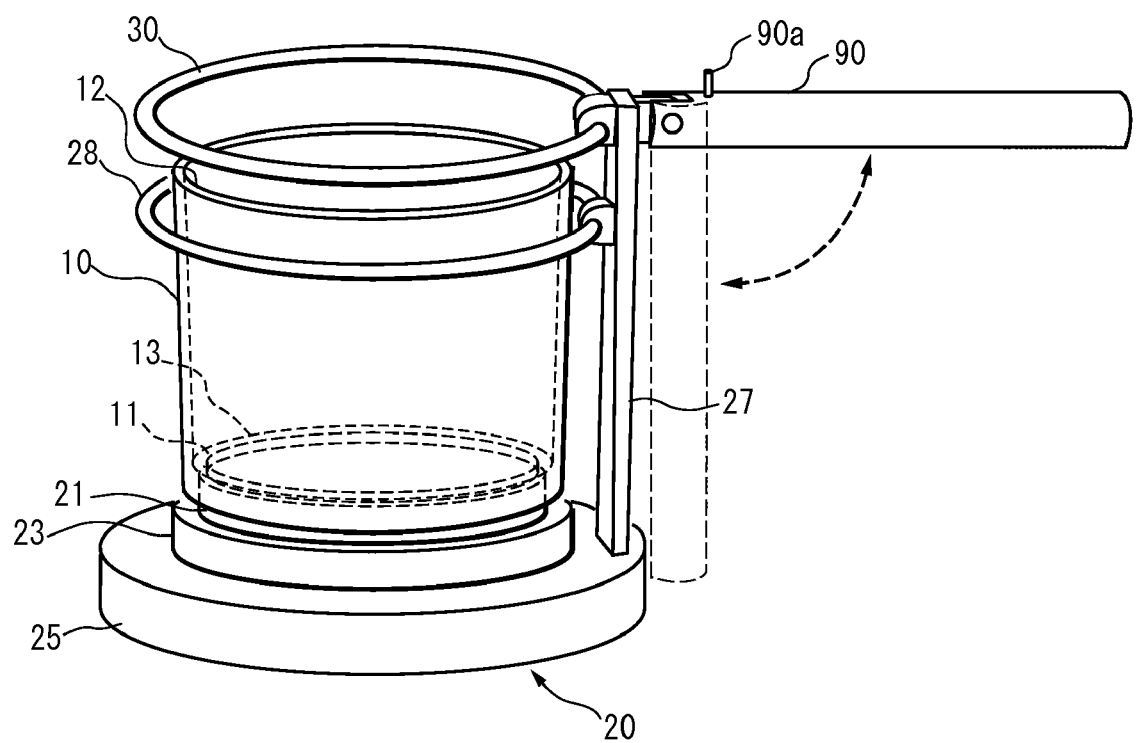
FIG. 9 is a perspective view showing a modified example in this embodiment.

Furthermore, in this embodiment, a horizontally extending rod-like holding portion 90 attached in a foldable manner may be provided on the attachment member 27 as shown in FIG. 9 instead of the holding portion 26. If this rod-like holding portion 90 is used, the hand holding the urine flow amount measuring apparatus is not practically wetted with urine splashed when being collected. When the urine flow amount measuring apparatus 100 is not being used, the holding portion 90 can be folded for compact storage. It is preferable that a portion to which the holding portion 90 is attached includes a lock mechanism with which the holding portion 90 can be locked so as to be kept horizontal. For example, the locked state can be cancelled by pressing a lock pin 90a in FIG. 9. FIG. 9 shows a case in which a columnar member having a rectangular cross section is used as the attachment member 27, but there is no limitation on the shape of the attachment member 27.

Furthermore, the urine flow amount measuring apparatus shown in this embodiment may further include one or more switches with which the user using this urine flow amount measuring apparatus can easily input a result of self-evaluation of a urine excretion state each time urine is excreted.

Figure 10:
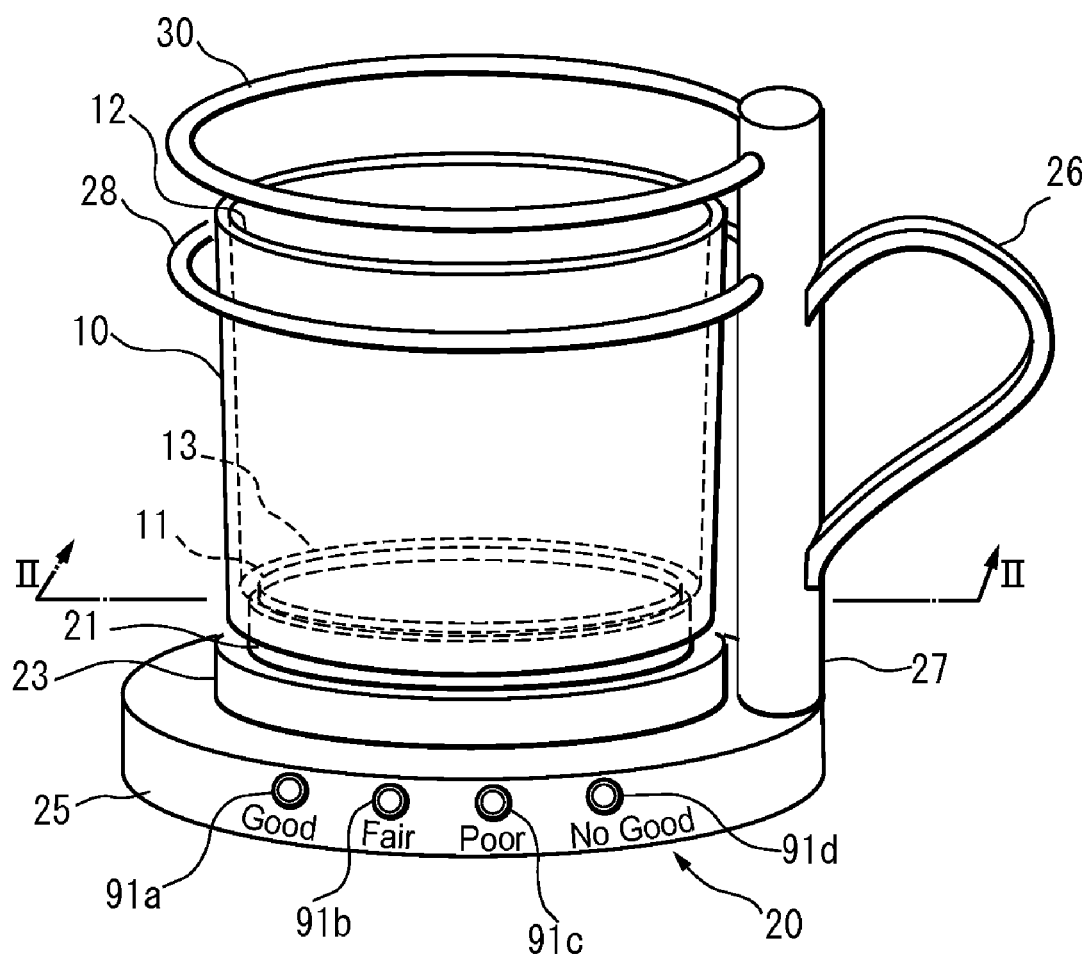
FIG. 10 is a perspective view showing a modified example in this embodiment.

FIG. 10 is a perspective view for showing the configuration of a modified example of the urine flow amount measuring apparatus according to this embodiment.

Figure 11:
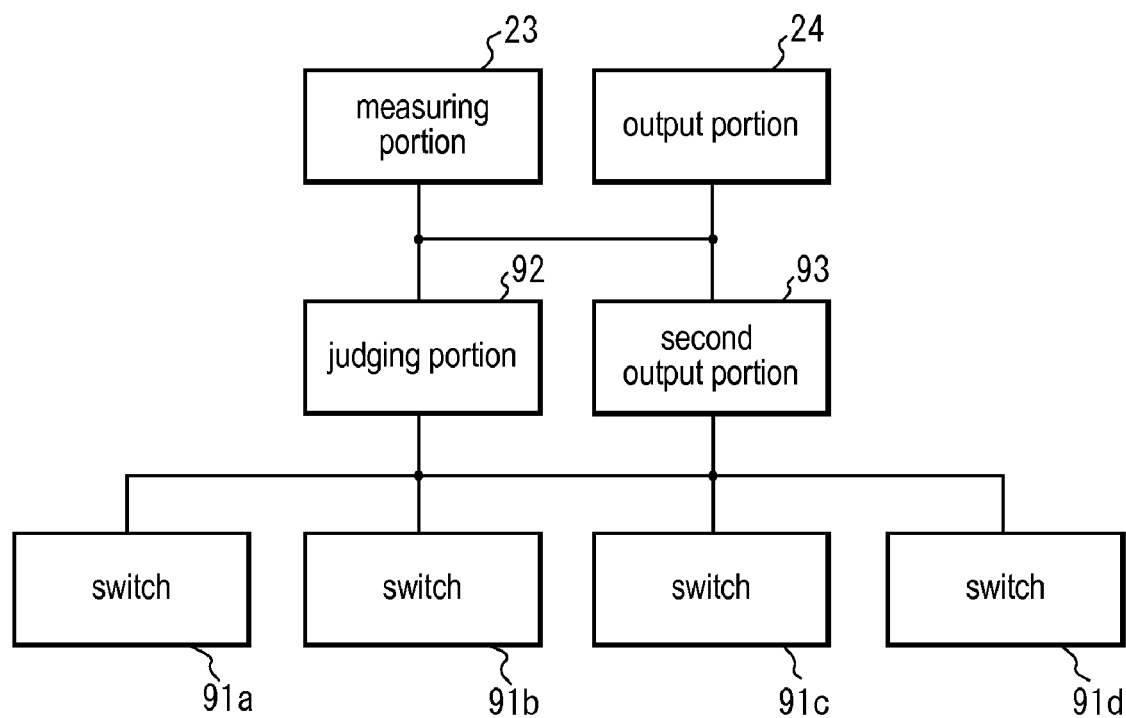
FIG. 11 is a block diagram showing the modified example in this embodiment.

FIG. 11 is a block diagram for showing the configuration of a modified example of the urine flow amount measuring apparatus according to this embodiment.

The urine flow amount measuring apparatus according to this modified example includes not only the measuring portion 23 and the output portion 24 as in the urine flow amount measuring apparatus 100 described above, but also four switches 91a to 91d, a judging portion 92, and a second output portion 93.

In this example, the switches 91a to 91d are pushbutton switches, and arranged on the fixing plate 25. For example, the switches 91a to 91d are associated with the evaluations 'Good', 'Fair', 'Poor', 'No Good'. If each of the switches 91a to 91d is turned on, in this example, if each of the switches 91a to 91d is pushed, a signal indicating an evaluation associated with each switch is output to the judging portion 92. The switches 91a to 91d are preferably pushbutton switches, but may be any switch such as slide switches, toggle switches, switches using touch sensors, or the like. Furthermore, there is no limitation on the position to which the switches 91a to 91d are arranged, as long as the operability is not impaired. In this example, four switches 91a to 91d are arranged, but the number of the switches may be any number of one or more. The number of the switches and the like may be set according to the number of evaluation items. Furthermore, the evaluations on urine excretion with which the switches are associated may be any evaluation. For example, the degree of urine excretion being good may be evaluated with a multiple-point scale. Furthermore, the switches may be associated with evaluation of pain or the like during urine excretion.

The judging portion 92 accepts an evaluation signal output from the switches 91a to 91d. It is judged whether or not the evaluation signal is accepted within a regular or irregular given period of time, for example, within five minutes after a time point when the measurement by the measuring portion 23 is performed. The time point when the measurement by the measuring portion 23 is performed refers to a time point when the measuring portion 23 starts detection of the weight, a time point when the measuring portion 23 ends detection, a specific time point or a given time point between these time points, or the like. Moreover, a time point when the power of the urine flow amount measuring apparatus is turned on may be regarded as the time point when the measurement is performed. There is no limitation on the position at which the judging portion 92 is situated. For example, the judging portion 92 is situated, for example, inside the fixing plate 25. The judging portion 92 is constituted by, for example, a calculating portion such as an MPU, a memory, and the like. Typically, the processing procedure of the judging portion 92 and the like are realized by software, and the software is stored in a storage medium such as a ROM. Note that the processing procedure and the like also may be realized by hardware (dedicated circuit).

The second output portion 93 accepts an evaluation signal output by the switches 91a to 91d, and outputs the accepted evaluation signal in association with information indicating the result of measurement performed by the measuring portion 23 output by the output portion 24. For example, the second output portion 93 accumulates the information indicating the result of measurement performed by the measuring portion 23 and the evaluation signal in association with each other in a removable memory card or the like. Herein, in particular, in a case where the judging portion 92 judges that the evaluation signal is accepted within a given period of time after a time point when the measurement by the measuring portion 23 is performed, the second output portion 93 outputs the evaluation signal in association with the information indicating the measurement result output by the output portion 24. In a case where the evaluation signal is output in association with the information indicating the measurement result output by the output portion 24, without considering whether or not the period of time after a time point when the measurement by the measuring portion 23 is performed is a given period of time or shorter, the judging portion 92 may be omitted.

Hereinafter, assuming that the given period of time is set to three minutes in advance in the judging portion 92, an operation of the urine flow amount measuring apparatus will be briefly described. First, the user measures a urine flow amount using this urine flow amount measuring apparatus. After the measurement of the urine flow amount ends, the user is required to input a result of self-evaluation of a urine excretion state during the measurement, by pushing any one of the switches 91a to 91d. More specifically, if urine excretion is satisfactory, the switch 91a indicating 'Good' is pushed. If urine excretion is neither very good nor very poor, and is normal, the switch 91b indicating 'Fair' is pushed. If urine excretion is insufficient, the switch 91c indicating 'Poor' is pushed. If urine excretion is not satisfactory at all, the switch 91d indicating 'No Good' is pushed. Then, signals associated with the respective switches are output from the switches 91*a* to 91*d*. Herein, for example, if the user pushes the switch 91*b* indicating 'Fair' as the result of self-evaluation of the latest urine excretion within one minute after the measurement of the urine flow amount, the judging portion 92 judges that the evaluation signal is accepted within a predetermined period of time, herein, three minutes, and the second output portion 93 outputs the evaluation information 'Fair' in association with the latest measurement result output from the output portion 24. As a result, the information 'Fair' is output, for example, displayed together with the measurement result of the urine flow amount or the measurement result of the urine flow rate. Furthermore, if the user forgets to input the result of self-evaluation of urine excretion and then pushes one of the switches 91*a* to 91*d*, for example, 30 minutes later, the judging portion 92 judges that the evaluation signal is not accepted within a predetermined period of time, herein, three minutes, and the second output portion 93 does not output the evaluation result.

Typically, in a case where a doctor or the like evaluates a urine excretion state of a user, not only data of the urine flow amount and the like, but also information of a result of self-evaluation such as user's impressions at the time of urine excretion is necessary. However, if the user is required to fill in a paper form about this result of self-evaluation, there is a problem in that information filled tends to be incomplete because filling such a paper form requires effort. Moreover, there is a problem in that the result of self-evaluation of the urine excretion state filled in the paper form has to be input again as data in association with data of the urine flow amount or the like in order to manage the result as data, and the input requires effort.

Conversely, according to the modified example, the urine flow amount measuring apparatus includes a configuration with which the result of self-evaluation of the urine excretion state can be input. Thus, the user can easily input impressions at the time of urine excretion immediately after the urine flow amount is measured. Furthermore, the measurement result of the urine flow amount and the result of self-evaluation of the urine excretion state can be output in association with each other, and thus the effort-requiring task of data input can be omitted.

Furthermore, if a given period of time has elapsed since the end of urine excretion, data indicating the result of self-evaluation of the user's urine excretion state is not output in association with the data indicating the measurement result of the urine flow amount. Thus, the result of self-evaluation of the urine excretion state can be prevented from being output erroneously in association with data other than the data indicating the latest measurement result of the urine flow amount. Furthermore, the user can be prevented from inputting data indicating erroneous result of self-evaluation of the urine excretion state based on vague memory after a long period of time after the urine flow amount is measured. As a result, a doctor or the like can be prevented from evaluating urine excretion of the user based on the data indicating the erroneous result of self-evaluation of the urine excretion state.

The present invention is not limited to the embodiment set forth herein. It will be appreciated that various modifications are possible within the scope of the present invention.

Industrial Applicability

As described above, the urine flow amount measuring apparatus according to the present invention is suitable as a urine flow amount measuring apparatus that measures a urine flow amount, and thus this apparatus is useful in particular as a portable urine flow amount measuring apparatus.

The invention claimed is:

1. A urine flow amount measuring apparatus, comprising:
a container that receives urine; and
a portable urine amount measuring device that measures the weight of the urine received by the container;
wherein the urine amount measuring device comprises:
a mounting plate, which is a plate on which the container is mounted;
a measuring portion that measures the weight of the container mounted on the mounting plate multiple times at given time intervals; and
an output portion that outputs a result of the measurement performed by the measuring portion, and
the urine flow amount measuring apparatus has a fixing structure using a magnet that is situated in at least a bottom portion of the container and a mounting face of the mounting plate and that detachably fixes the container on the mounting plate.

2. The urine flow amount measuring apparatus according to claim 1, wherein the fixing structure is constituted by a magnetic metal that is situated on the mounting face side of the container and a magnet that is situated on the mounting face side of the mounting plate.

3. The urine flow amount measuring apparatus according to claim 1, further comprising a protecting portion that restricts a horizontal movement of the container in a state where the container is mounted on the mounting plate.

4. The urine flow amount measuring apparatus according to claim 1, further comprising a holding portion that is used for holding the measuring portion.

5. The urine flow amount measuring apparatus according to claim 1, further comprising a guard portion that is situated above the container along an opening portion of the container.

6. The urine flow amount measuring apparatus according to claim 1,
wherein an upper portion of the mounting plate has a projection face,
a bottom face of the container has a recessed face, and
the recessed face is mounted so as to cover the projection face of the mounting plate.

7. The urine flow amount measuring apparatus according to claim 1, wherein the output portion performs a given calculation on the result of the measurement performed by the measuring portion, and outputs a result of the calculation.

8. A urine flow amount measuring apparatus, comprising:
a container that receives urine; and
a portable urine amount measuring device that measures the weight of the urine received by the container;
wherein the urine amount measuring device comprises:
a mounting plate, which is a plate on which the container is mounted;
a measuring portion that measures the weight of the container mounted on the mounting plate multiple times at given time intervals; and
an output portion that outputs a result of the measurement performed by the measuring portion, and
the urine flow amount measuring apparatus has a fixing structure using hook-and-loop fasteners that is situated in at least a bottom portion of the container and a mounting face of the mounting plate and that detachably fixes the container on the mounting plate.

* * * * *